United States Patent
Uang et al.

(10) Patent No.: US 8,168,835 B2
(45) Date of Patent: May 1, 2012

(54) METHOD FOR PREPARING PROPARGYLIC ALCOHOL CATALYZED BY 2-MORPHOLINOISOBORNANE-10-THIOL

(75) Inventors: Biing-Jiun Uang, Hsinchu (TW); Ping-Yu Wu, Hsinchu (TW); Hsyueh-Liang Wu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 161 days.

(21) Appl. No.: 12/787,961

(22) Filed: May 26, 2010

(65) Prior Publication Data

US 2011/0295042 A1 Dec. 1, 2011

(51) Int. Cl.
  *C07C 41/18* (2006.01)
  *C07C 29/36* (2006.01)

(52) U.S. Cl. ........... 568/649; 568/807

(58) Field of Classification Search ......... 568/649, 568/807
See application file for complete search history.

(56) References Cited

OTHER PUBLICATIONS

Ping-Yu Wu, Hsyueh-Liang Wu, Ying-Ying Shen, and Biing-Jiun Uang; Asymmetric Synthesis of Propargylic Alcohols Catalyzed by (-)-MITH; Tetrahedron:Asymmetry 20; Sep. 2, 2009; pp. 1837-1841.

*Primary Examiner* — Sikarl Witherspoon
(74) *Attorney, Agent, or Firm* — Muncy, Geissler, Olds & Lowe, PLLC

(57) ABSTRACT

A method for preparing a propargylic alcohol catalyzed by 2-morpholinoisobornane-10-thiol (MITH) is disclosed, which includes reacting $R_1CHO$ with $R_2CCH$ in the presence of $R_3ZnR_4$ and MITH, wherein each of $R_1$, $R_2$, $R_3$, and $R_4$, independently, is optionally substituted alkyl, alkenyl, cycloalkyl, cycloalkenyl, alkylsilyl, heterocycloalkyl, heterocycloalkenyl, aryl, aryloxy, or heteroaryl. The method can give enantioenriched propargylic alcohols with good enantioselective at low loading of MITH.

20 Claims, No Drawings

METHOD FOR PREPARING PROPARGYLIC ALCOHOL CATALYZED BY 2-MORPHOLINOISOBORNANE-10-THIOL

BACKGROUND OF THE INVENTION

1. Field of the Invention

The present invention relates to a method for preparing a propargylic alcohol catalyzed by 2-morpholinoisobornane-10-thiol (MITH).

2. Description of Related Art

Chiral propargylic alcohols are versatile building blocks for the synthesis of optically active pharmaceutical ingredients and natural products. The following Table 1 exemplifies some applications of propargylic alcohols.

TABLE 1

| Entry | Starting block | Synthetic product | Remark |
|---|---|---|---|
| 1 | | | Chondrillin, an anticancer natural product |
| 2 | | | Pesticide |
| 3 | | | (−)-Chlorothricolide, an aglycone of chlorothricin which is an antibiotic capable of inhibiting biosynthesis of cholesterol |
| 4 | | | (+)-Spirolaxine, isolated from fungi, being able to reduce the amount of cholesterol, and toxic to endothelial and tumor cells |

TABLE 1-continued

| Entry | Starting block | Synthetic product | Remark |
|---|---|---|---|
| 5 | 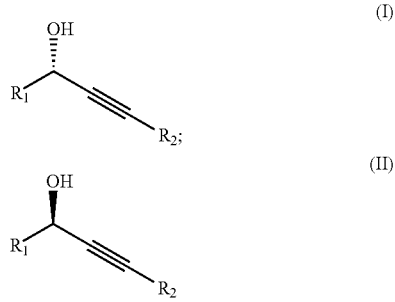 | | (−)-Scopadulcic Acid A, extracted from *Scrophularia L.*, being helpful to digestion and protective to digestive system |

Among the several efficient procedures that have been developed, such as Ti-mediated reactions, there is a particular emphasis on the asymmetric nucleophilic addition of Zn-alkynylides to carbonyl compounds to prepare enantioenriched propargylic alcohols, which offer the advantages of the low-toxicity of zinc metal and the wide functional group tolerance of organozinc reagents. In literature reports describing the asymmetric addition of Zn-alkynylides to aldehydes, preparing the corresponding propargylic alcohols in high enantiomeric excess (ee) usually requires high ligand loadings. Thus, it is desirable to develop a method for preparing propargylic alcohols with an effective chiral mediator that promotes the enantioselective alkynylation of aldehydes at lower ligand loading.

SUMMARY OF THE INVENTION

The object of the present invention is to provide a method for preparing a propargylic alcohol catalyzed by 2-morpholinoisobornane-10-thiol (MITH), comprising reacting $R_1CHO$ with $R_2CCH$ in the presence of $R_3ZnR_4$ and MITH, wherein each of $R_1$, $R_2$, $R_3$, and $R_4$, independently, is optionally substituted alkyl, alkenyl, cycloalkyl, cycloalkenyl, alkylsilyl, heterocycloalkyl, heterocycloalkenyl, aryl, aryloxy, or heteroaryl. The method of the present invention can provide compounds of formulas (I) and (II) when (−)-2-exo-morpholinoisobornane-10-thiol((−)-MITH) and (+)-2-endo-morpholinoisobornane-10-thiol((+)-MITH) are used as the chiral ligands, respectively.

(I)

(II)

Preferably, each of $R_1$ and $R_2$, independently, is $C_{1-30}$ alkyl optionally substituted by one or more of halogen, nitro, cyano, 5-14 membered heteroaryl, $C_{6-14}$ aryl, $C_{6-14}$ aryloxy, $C_{1-30}$ alkoxy, $C_{1-30}$ haloalkyl, $CO_2$—$C_{1-30}$ alkyl, $CO_2$—$C_{2-30}$ alkenyl, and $C_{1-30}$ alkylsilyloxy; $(CH_2)_tR_a$; $C_{2-30}$ alkenyl optionally substituted by one or more of halogen, nitro, cyano, 5-14 membered heteroaryl, $C_{6-14}$ aryl, $C_{6-14}$ aryloxy, $C_{1-30}$ alkoxy, $C_{1-30}$ haloalkyl, $CO_2$—$C_{1-30}$ alkyl and $CO_2$—$C_{2-30}$ alkenyl; $(CH_2)_tCH=CH(CH_2)_kR_a$; $C_{5-14}$ cycloalkyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; $C_{5-14}$ cycloalkenyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; 5-14 membered heterocycloalkyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; 5-14 membered heterocycloalkenyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; $C_{6-14}$ aryl optionally substituted by one or more of halogen, nitro, cyano, $C_{1-30}$ alkyl, $C_{2-30}$ alkenyl, $C_{1-30}$ alkoxy, $C_{1-30}$ haloalkyl, $C_{6-14}$ aryloxy, $CO_2$—$C_{1-30}$ alkyl, and $CO_2$—$C_{2-30}$ alkenyl; $C_{1-30}$ alkylsilyl optionally substituted by one or more of halogen, nitro, and cyano; or 5-14 membered heteroaryl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl, and $CO_2$—$C_{2-30}$ alkenyl; and each of $R_3$ and $R_4$ independently is $C_{1-30}$ alkyl optionally substituted by one or more of halogen, nitro, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; $C_{2-30}$ alkenyl optionally substituted by one or more of halogen, nitro, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and $C_{5-14}$ heteroaryl; $C_{5-14}$ cycloalkyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; $C_{5-14}$ cycloalkenyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; 5-14 membered heterocycloalkyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; 5-14 membered heterocycloalkenyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; $C_{6-14}$ aryl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or 5-14 membered heteroaryl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl, wherein $R_a$ is $C_{6-14}$ aryl substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; $C_{1-30}$ alkylsilane optionally substituted by one or more of halogen, nitro, cyano, $C_{1-30}$ alkoxy, $CO_2$—$C_{1-30}$ alkyl, and $CO_2$—$C_{2-30}$ alkenyl; or 5-14 membered heteroaryl substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; i is an integer of 1 to 30; and each of r and k independently is an integer of 0 to 30.

More preferably, each of $R_1$ and $R_2$, independently, is $C_{1-16}$ alkyl optionally substituted by one or more of halogen, nitro, cyano, 5-14 membered heteroaryl, $C_{6-14}$ aryl, $C_{6-14}$ aryloxy, $C_{1-16}$ alkoxy, $C_{1-16}$ haloalkyl, $CO_2$—$C_{1-16}$ alkyl, $CO_2$—$C_{2-16}$ alkenyl, and $C_{1-16}$ alkylsilyloxy; $(CH_2)_iR_a$; $C_{2-16}$ alkenyl optionally substituted by one or more of halogen, nitro, cyano, 5-14 membered heteroaryl, $C_{6-14}$ aryl, $C_{6-14}$ aryloxy, $C_{1-16}$ alkoxy, $C_{1-16}$ haloalkyl, $CO_2$—$C_{1-16}$ alkyl and $CO_2$—$C_{2-16}$ alkenyl; $(CH_2)_rCH=CH(CH_2)_kR_a$; $C_{5-14}$ cycloalkyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; $C_{5-14}$ cycloalkenyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; 5-14 membered heterocycloalkyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; 5-14 membered heterocycloalkenyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; $C_{6-14}$ aryl optionally substituted by one or more of halogen, nitro, cyano, $C_{1-16}$ alkyl, $C_{2-16}$ alkenyl, $C_{1-16}$ alkoxy, $C_{1-16}$ haloalkyl, $C_{6-14}$ aryloxy, $CO_2$—$C_{1-16}$ alkyl, and $CO_2$—$C_{2-16}$ alkenyl; $C_{1-16}$ alkylsilyl optionally substituted by one or more of halogen, nitro, and cyano; or 5-14 membered heteroaryl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl, and $CO_2$—$C_{2-16}$ alkenyl; and each of $R_3$ and $R_4$ independently is $C_{1-16}$ alkyl optionally substituted by one or more of halogen, nitro, cyano, $C_{1-16}$ alkoxy, $C_{1-16}$ haloalkyl, $CO_2$—$C_{1-16}$ alkyl, $CO_2$—$C_{2-16}$ alkenyl, $C_{6-14}$ aryl and 5-14 membered heteroaryl; $C_{2-16}$ alkenyl optionally substituted by one or more of halogen, nitro, cyano, $C_{1-16}$ alkoxy, $C_{1-16}$ haloalkyl, $CO_2$—$C_{1-16}$ alkyl, $CO_2$—$C_{2-16}$ alkenyl, $C_{6-14}$ aryl and $C_{5-14}$ heteroaryl; $C_{5-14}$ cycloalkyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; $C_{5-14}$ cycloalkenyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; 5-14 membered heterocycloalkyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; 5-14 membered heterocycloalkenyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; $C_{6-14}$ aryl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; or 5-14 membered heteroaryl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl, wherein $R_a$ is $C_{6-14}$ aryl substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-46}$ alkenyl; $C_{1-16}$ alkylsilane optionally substituted by one or more of halogen, nitro, cyano, $C_{1-16}$ alkoxy, $CO_2$—$C_{1-16}$ alkyl, and $CO_2$—$C_{2-16}$ alkenyl; or 5-14 membered heteroaryl substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; i is an integer of 1 to 16; and each of r and k independently is an integer of 0 to 16.

In one aspect of the method, $R_2$ is $C_{6-14}$ aryl optionally substituted by one or more of halogen, $C_{1-16}$ haloalkyl, and $C_{1-16}$ alkoxy, and $R_1$ is $(CH_2)_iR_a$, in which $R_a$ is $C_{6-14}$ aryl and i is an integer of 1 to 5.

In another aspect of the method, $R_2$ is $C_{6-14}$ aryl optionally substituted by one or more of halogen, $C_{1-16}$ haloalkyl, and $C_{1-16}$ alkoxy, and $R_1$ is $C_{6-14}$ aryl optionally substituted by one or more of halogen, $C_{1-16}$ haloalkyl, and $C_{1-16}$ alkoxy.

In still another aspect of the method, $R_2$ is $C_{6-14}$ aryl optionally substituted by one or more of halogen, $C_{1-16}$ haloalkyl, and $C_{1-16}$ alkoxy, and $R_1$ is $(CH_2)_rCH=CH(CH_2)_kR_a$, in which $R_a$ is $C_{6-14}$ aryl, and r and k respectively are 1 and 0.

In further another aspect of the method, $R_2$ is $C_{6-14}$ aryl optionally substituted by one or more of halogen, $C_{1-16}$ haloalkyl, and $C_{1-16}$ alkoxy, and $R_1$ is $C_{2-16}$ alkenyl optionally substituted by one or more of $C_{6-14}$ aryl and $C_{1-16}$ alkyl.

In yet another aspect of the method, $R_2$ is $C_{1-16}$ alkyl, and $R_1$ is $C_{6-14}$ aryl.

In the method of the present invention, a solvent used can be selected from a group consisting of toluene, hexane, hexane-tetrahydrofuran, toluene-dichloromethane, toluene-dioxane, toluene-diethyl ether, and toluene-tetrahydrofuran. Preferably, the mixture of toluene-tetrahydrofuran is used as the solvent. In this regard, a volume ratio of toluene to tetrahydrofuran can be in a range from 0.5 to 10. Preferably, the volume ratio thereof is in a range from 3 to 9.

In the method of the present invention, a molar ratio of $R_3ZnR_4$ to $R_2CCH$ can be in a range from 0.25 to 4. Preferably, the molar ratio of $R_3ZnR_4$ to $R_2CCH$ is in a range from 0.5 to 2. Besides, $R_2CCH$ and $R_3ZnR_4$ can be respectively used in an amount of 1 to 8 equivalents based on $R_1CHO$.

In the method of the present invention, $R_2CCH$ is reacted first with $R_3ZnR_4$ and then with $R_1CHO$. In other words, it is necessary to react $R_2CCH$ with $R_3ZnR_4$ for a period of time so as to afford zinc acetylides, and then to proceed with the reaction between zinc acetylides and $R_1CHO$ to give propargylic alcohols. Preferably, a temperature of the reaction with $R_3ZnR_4$ is controlled in a range from 10° C. to 70° C., and a temperature of the reaction with $R_1CHO$ is controlled in a range from −30° C. to 40° C.

In regard to a used amount of MITH, 0.1~10 mol % based on $R_2CCH$ is preferable. Besides, (−)-2-exo-morpholinoisobornane-10-thiol((−)-MITH) can be used as MITH in the method of the present invention. In this case, S-form propargylic alcohols may be prepared in the majority. In the other hand, if (+)-2-endo-morpholinoisobornane-10-thiol ((+)-MITH) is used as MITH, R-form propargylic alcohols may be prepared in the majority.

Referring to a used amount of $R_2CCH$ and $R_3ZnR_4$, 1 to 8 equivalents based on $R_1CHO$ are preferable, respectively.

The term "alkyl" refers to a straight or branched hydrocarbon. Examples of alkyl include, but are not limited to, methyl, ethyl, n-propyl, i-propyl, n-butyl, i-butyl, and t-butyl.

The term "alkenyl" refers to a straight or branched hydrocarbon containing one or more double bonds. Examples of alkenyl, but are not limited to, include ethenyl, propenyl, allyl, and 1,4-butadienyl.

The term "cycloalkyl" refers to a saturated hydrocarbon ring system. Examples of cycloalkyl include, but are not limited to, cyclopropyl, cyclobutyl, cyclopentyl, cyclohexyl, cycloheptyl, and cyclooctyl.

The term "cycloalkenyl" refers to a non-aromatic hydrocarbon ring system having one or more double bonds. Examples of cycloalkenyl include, but are not limited to, cyclopentenyl, cyclohexenyl, and cycloheptenyl.

The term "heterocycloalkyl" refers to a saturated hydrocarbon ring system having at least one ring heteroatom (e.g., N, O, S or Se). Examples of heterocycloalkyl include, but are not limited to, 4-tetrahydropyranyl.

The term "heterocycloalkenyl" refers to a non-aromatic hydrocarbon ring system having at least one ring heteroatom (e.g., N, O, S or Se) and at least one ring double bond. Examples of heterocycloalkenyl include, but are not limited to, pyranyl.

The term "aryl" refers to an aromatic ring system, which may be a 6-carbon monocyclic, 10-carbon bicyclic, 14-carbon tricyclic aromatic ring system. Examples of aryl groups include, but are not limited to, phenyl, naphthyl, and anthracenyl.

The term "heteroaryl" refers to an aromatic ring system having one or more heteroatoms (such as O, N, S, or Se), which may be a 5 monocyclic, 8-12 membered bicyclic, or 11-14 membered tricyclic aromatic ring system having one or more heteroatoms. Examples of heteroaryl groups include pyridyl, furyl, imidazolyl, benzimidazolyl, pyrimidinyl, thienyl, quinolinyl, indolyl, and thiazolyl.

The term "alkylsilyl" refers to

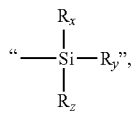

in which each of $R_x$, $R_y$, and $R_z$ is alkyl, independently.

The term "aryloxy" refers to "—O-aryl", and the term "alkoxy" refers to "—O-alkyl". Besides, the term "alkylsilyloxy" refers to

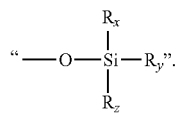

The above-mentioned alkyl, alkenyl, cycloalkyl, cycloalkenyl, heterocycloalkyl, heterocycloalkenyl, alkylsilyl, aryloxy, alkoxy, alkylsilyloxy, aryl and heteroaryl include both substituted and unsubstituted moieties. The term "substituted" refers to one or more substituents (which may be the same or different), each replacing a hydrogen atom. Examples of substituents include, but are not limited to, halogen (such as F, Cl, Br or I), hydroxyl, amino, alkylamino, arylamino, dialkylamino, diarylamino, cyano, nitro, mercapto, carbonyl, carbamido, carbamyl, carboxyl, thioureido, thiocyanato, sulfoamido, alkyl, alkenyl, alkoxy, haloalkyl (i.e. alkyl substituted by one or more halogen atoms), aryl, heteroaryl, cyclyl, heterocyclyl, $CO_2$-alkyl and $CO_2$-alkenyl. Among these above-mentioned substituents, alkyl, alkenyl, alkoxy, aryl, heteroaryl, cyclyl, and heterocyclyl are optionally further substituted with, for example, alkyl, alkenyl, alkoxy, haloalkyl, aryl, heteroaryl, halogen, hydroxyl, amino, mercapto, cyano, nitro, $CO_2$-alkyl or $CO_2$-alkenyl.

Other objects, advantages, and novel features of the invention will become more apparent from the following detailed description when taken in conjunction with the accompanying drawings.

BRIEF DESCRIPTION OF THE DRAWINGS

None.

DETAILED DESCRIPTION OF THE PREFERRED EMBODIMENT

Examples I-1 to I-4

Trial Preparation of (1S)-1,3-diphenyl-prop-2-yn-1-ol (Compound 3)

Initially, the preparation of zinc acetylide from phenylacetylene 2 and dimethylzinc was examined for the method of the present invention. In accordance with the following Scheme I and the reaction conditions listed in Table I, in the presence of ligand 1 ((−)-2-exo-morpholinoisobornane-10-thiol((−)-MITH), 10 mol %), deprotonation of compound 2 at 70° C. or room temperature in toluene, hexane, or a mixture of toluene-tetrahydrofuran (TOL-THF) followed by the addition of benzaldehyde at −30° C. or 0° C., gave alkynylation product 3.

Scheme I

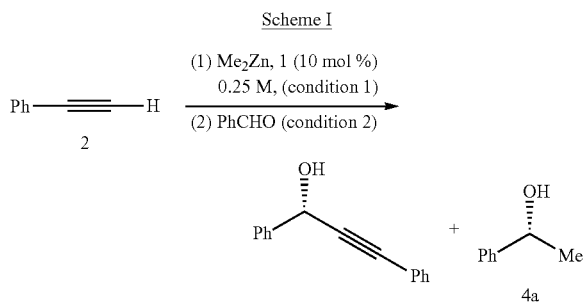

TABLE I

|  |  |  | Condition 1 | | Condition 2 | | 3 | | 4a |
|---|---|---|---|---|---|---|---|---|---|
| Example | Me₂Zn (equiv) | 2 (equiv) | Solvent | Temp (° C.) | Time (h) | Temp (° C.) | Time (h) | Yield[a] (%) | ee[b] (%) | Yield[c] (%) |
| I-1[d] | 6 | 7 | Toluene | 70 | 2.5 | −30 | 24 | 66 | 39 | <5 |
| I-2 | 3 | 3 | Hexane | rt | 0.5 | 0 | 13 | 37 | 68 | 43 |

TABLE I-continued

| Example | Me$_2$Zn (equiv) | 2 (equiv) | Solvent | Condition 1 Temp (°C) | Condition 1 Time (h) | Condition 3 Temp (°C) | Condition 3 Time (h) | Yield$^a$ (%) | ee$^b$ (%) | 4a Yield$^c$ (%) |
|---|---|---|---|---|---|---|---|---|---|---|
| I-3 | 3 | 3 | Toluene | rt | 0.5 | 0 | 13 | 39 | 62 | 40 |
| I-4 | 3 | 3 | TOL-THF$^e$ | rt | 2 | 0 | 28 | 80 | 81 | ND$^f$ |

$^a$Isolated yield after column chromatography
$^b$Determination by chiral HPLC.
$^c$Yield determined by crude $^1$H NMR.
$^d$The reaction was conducted in 0.125M.
$^e$TOL-THF = toluene/THF = 1.5:1 (v/v).
$^f$Not detected by $^1$H NMR.

With reference to Table I, Compound 3 was obtained predominantly in Example I-1, albeit, with a modest yield and low enantiomeric excess (ee). In addition, although deprotonation at ambient temperature in either toluene or hexane led to unsatisfactory yields, and the methylated adduct 4a was obtained as the major product (Examples I-2 and I-3), preparation of Compound 3 was still achieved. Regarding the results shown in Table I, a better yield with higher ee in which no methylation product was observed (Example I-4) was obtained in a mixed TOL-THF solvent system.

(1S)-1,3-Diphenyl-prop-2-yn-1-ol (Compound 3)

A colorless oil. $[\alpha]_D^{27}$ −2.4 (c 1.2, CHCl$_3$); $^1$H NMR (400 MHz, CDCl$_3$): δ 7.62-7.60 (m, 2H), 7.48-7.45 (m, 2H), 7.42-7.29 (m, 2H), 5.68 (d, J=6.0 Hz, 1H), 2.32 (d, J=6.0 Hz, 1H); $^{13}$C NMR (100 MHz, CDCl$_3$): δ 140.6 (C), 131.6 (CH×2), 128.5 (CH×2), 128.4 (CH), 128.2 (CH), 128.2 (CH×2), 126.6 (CH×2), 122.3 (C), 88.8 (C), 86.5 (C), 64.9 (CH); IR (neat) 3365, 3062, 3032, 2872, 2229, 1955, 1885, 1809, 1749, 1598, 1490, 1455, 1031, 757, 692 cm$^{-1}$; HRMS calculated for C$_{15}$H$_{12}$O 208.0888, found 208.0882. Chiral HPLC analysis: Chiralcel OD-H, 2-propanol/hexane (10:90), 1.0 mL/min, uv 254 nm; t$_R$=10.7 min (7.0%), 19.6 min (93.0%), 86% ee.

Examples II-1 to II-7

Optimization of the Reagent Equivalents

The equivalents of zinc acetylide were subsequently optimized to achieve a better enantioselectivity with the toluene-THF (1.5:1) mixed solvent system according to Scheme II and the parameters of Table II.

Scheme II

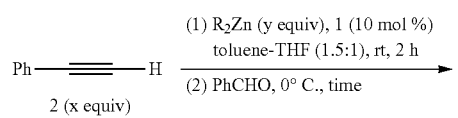

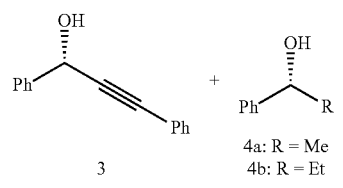

TABLE II

| Example | R | x | y | Time (h) | 3 Yield$^a$ (%) | 3 ee$^b$ (%) | 4 yield$^c$ (%) |
|---|---|---|---|---|---|---|---|
| II-1 | Me | 1.5 | 1.5 | 36 | 93 | 70 | ND |
| II-2 | Me | 2 | 2 | 36 | 98 | 69 | ND |
| II-3 | Me | 4 | 4 | 28 | 85 | 82 | ND |
| II-4 | Me | 8 | 8 | 36 | 94 | 81 | ND |
| II-5 | Me | 4 | 8 | 21 | 91 | 80 | ND |
| II-6 | Me | 4 | 2 | 48 | 85 | 81 | ND |
| II-7 | Et | 4 | 4 | 22 | 80 | 79 | 19 |

$^a$Isolated yield after column chromatography
$^b$Determination by chiral HPLC.
$^c$Yield determined by crude $^1$H NMR. ND: not detected by $^1$H NMR.

In accordance with the results of Table II, the reaction gave better ee when more than 4 equiv of organozincs were used (Examples II-1 and II-2 vs Examples II-3 to II-7). Although it was reported that a 1:1 mixture of alkynyl and dialkylzinc gave the propargylic alcohols in higher ee, adducts with comparable ee's were observed in these cases under different ratios of dimethylzinc to phenylacetylene (Examples II-3, II-5, and II-6). Alkylation product 4b was obtained when dimethylzinc was substituted with diethylzinc (Example II-7). Accordingly, 4 equiv of methylalkynylzinc for economical concern were applied for further optimization of solvents (Example II-3).

Examples III-1 to III-8

Optimization of the Solvent System

Over re-examination of the solvent effect was first focused on the role of tetrahydrofuran. After the zinc acetylide was prepared in TOL-THF (1.5:1), the solvents were removed and the addition reaction was performed in toluene since the ether solvent was considered to promote the background reaction. The reaction accorded with Scheme III and the parameters of Table III.

Scheme III

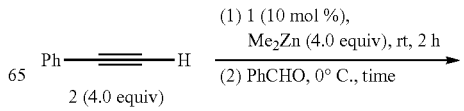

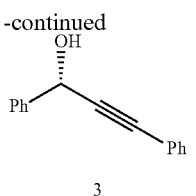

3 + 4a

TABLE III

| Example | Solvent[a] | Time (h) | Yield[b] (%) | ee[c] (%) | yield[d] (%) |
|---|---|---|---|---|---|
| III-1 | Toluene | 21 | 82 | 8 | ND |
| III-2[e] | HEX-THF (1.5:1) | 38 | 90 | 79 | ND |
| III-3 | TOL-DCM (1.5:1) | 24 | 61 | 64 | 17 |
| III-4 | TOL-DOX (1.5:1) | 28 | 93 | 74 | ND |
| III-5 | TOL-DEE (1.5:1) | 28 | 83 | 49 | 12 |
| III-6 | TOL-THF (1:2) | 96 | 74 | 76 | ND |
| III-7 | TOL-THF (3:1) | 24 | 94 | 83 | ND |
| III-8 | TOL-THF (9:1) | 22 | 94 | 77 | 5 |

[a]Solvent abbreviations: TOL—toluene; THF—tetrahydrofuran; HEX—hexane; DCM—dichloromethane; DOX—dioxane; and DEE—diethyl ether
[b]Isolated yield after column chromatography.
[c]Determined by chiral HPLC.
[d]Yield determined by crude $^1$H NMR; ND: not detected by $^1$H NMR.
[e]Me$_2$Zn (0.7M in hexane) was used; the reaction was conducted in 0.10M with respect to PhCHO.

In accordance with the results shown in Table III, the absence of tetrahydrofuran in the system delivered quite low ee (Table III, Example III-1 vs Table II, Example II-3). Changing the reaction medium from TOL-THF to HEX-THF was not beneficial to the ee and yield (Example III-2). Using other solvents in place of tetrahydrofuran with toluene gave no better results (Examples III-3 to III-5). Thus, co-solvent mixtures of toluene and tetrahydrofuran with different ratios were tested. A ratio of 3:1 was found to be a better solvent system for the asymmetric addition of phenylethynyl zinc to benzaldehyde, and (1S)-1,3-diphenylprop-2-yn-1-ol 3 was isolated in 94% yield and 83% ee (Example III-7).

Examples VI-1 to VI-8

Optimization of Temperature and Ligand Loadings

Reactions with PhCHO in different amounts of the ligand 1 at varied temperatures for various periods of time were performed according to Scheme VI and the parameters of Table VI.

Scheme VI

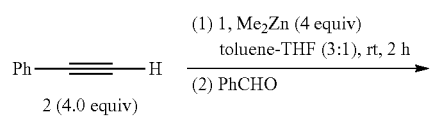

(1) 1, Me$_2$Zn (4 equiv)
toluene-THF (3:1), rt, 2 h
(2) PhCHO

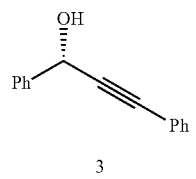

3

TABLE VI

| Example | 1 (mol %) | Temp (h) | Time (h) | Yield[a] (%) | ee[b] (%) |
|---|---|---|---|---|---|
| VI-1 | 10 | rt | 6 | 91 | 76 |
| VI-2 | 10 | 10 | 16 | 99 | 79 |
| VI-3 | 10 | 10 | 24 | 91 | 84 |
| VI-4 | 10 | −20 | 24 | 75 | 87 |
| VI-5 | 10 | −30 | 72 | 61 | 90 |
| VI-6 | 5 | −20 | 42 | 73 | 86 |
| VI-7 | 2.5 | −20 | 48 | 61 | 84 |
| VI-8 | 1 | −20 | 72 | 73 | 51 |

[a]Isolated yield after column chromatography; methylation product was observed in <5% yield by crude $^1$H NMR in all cases
[b]Determined by chiral HPLC.

As the results shown in Table VI, conducting the reactions at low temperature enhanced the enantioselectivities (Table VI, Examples VI-1 to VI-5) with the best result of 87% ee along with 75% yield (Example VI-4). A better enantioselectivity (90% ee) was obtained at −30° C. (Example VI-5), but the yield was low and a longer reaction time was necessary. However, as the ligand loading decreased to 2.5 mol %, a slightly deteriorated enantioinduction was observed. In general, 87-84% ee's were observed through 10-2.5 mol % of ligand 1 at −20° C. (Examples VI-4 and VI-6 to VI-8).

Examples V-1 to V-14

Optimization of Additive Addition Based on 2.5 mol % of Ligand 1

After obtaining good enantioselectivity in the alkynylation of benzaldehyde with only 2.5 mol % of ligand 1 in the abovementioned Example, the attention was then turned to the effects of additives. According to Scheme V and Table V, additives such as isopropanol (Examples V-1 to V-6) and alkyl borates (Examples V-7 to V-10) were investigated to improve the asymmetric induction because they have been reported to accelerate similar catalytic organozinc reactions, and added.

Scheme V

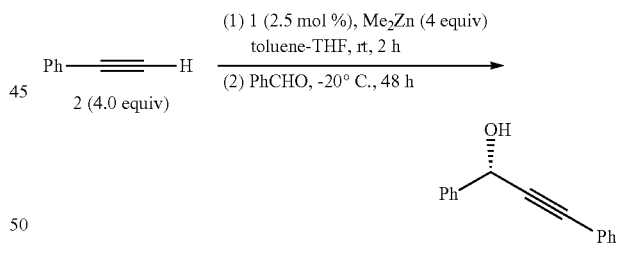

TABLE V

| Example | TOL-THF | Additive[a] | Yield[b] (%) | ee[c] (%) |
|---|---|---|---|---|
| V-1 | 3:1 | 2.5 mol % i-PrOH | 61 | 65 |
| V-2 | 3:1 | 5 mol % i-PrOH | 58 | 62 |
| V-3 | 3:1 | 10 mol % i-PrOH | 63 | 76 |
| V-4 | 3:1 | 25 mol % i-PrOH | 62 | 74 |
| V-5 | 3:1 | 50 mol % i-PrOH | 66 | 72 |
| V-6 | 3:1 | 100 mol % i-PrOH | 55 | 67 |
| V-7 | 3:1 | 10 mol % B(OEt)$_3$ | 67 | 82 |
| V-8 | 3:1 | 10 mol % B(Oi-Pr)$_3$ | 52 | 87 |
| V-9 | 3:1 | 10 mol % B(Ot-Bu)$_3$ | 55 | 87 |
| V-10[d] | 3:1 | 10 mol % B(Ot-Bu)$_3$ | 70 | 79 |

TABLE V-continued

| Example | TOL-THF | Additive[a] | Yield[b] (%) | ee[c] (%) |
|---|---|---|---|---|
| V-11 | 4:1 | — | 59 | 87 |
| V-12 | 5:1 | — | 68 | 86 |
| V-13 | 7:1 | — | 61 | 85 |
| V-14 | 9:1 | — | 55 | 83 |

[a]Additives were added to the reaction mixture after step 1
[b]Isolated yield after column chromatography; methylation product was observed in <5% yield under crude 1H NMR in all cases.
[c]Determined by chiral HPLC.
[d]8 equiv of alkyne were used.

Based on the results of Table V, the addition of isopropanol as well as a variety of borates in catalytic to stoichiometric amounts showed no improvement in the ee of the adduct. Nevertheless, perhaps the TOL-THF solvent system was not suitable for the addition of additives in the reaction, and thus the change of the solvent system might enable the addition of the additives to afford the aforesaid improvement. Besides, the ratio of the mixed solvent system was examined again at −20° C. (Examples V-11 to V-14), and it was found that a slightly lower percentage of THF in the co-solvent system could enhance the yield without a loss of ee (Example V-12).

Examples VI-1 to VI-15

Asymmetric Alkynylation of Various Aldehydes Catalyzed by 2.5 mol % of Ligand 1

The scope of this catalytic system was investigated to include a variety of aldehydes according to Scheme VI and the parameters of Table VI. The detailed steps of the reactions are described as follows: A flame-dried 10-mL flask containing (−)-MITH (6.4 mg, 0.025 mmol, 2.5 mol %) was filled with argon. The flask was added sequentially tetrahedronfuran (667 μL), dimethylzinc (3.3 mL, 4 mmol, 1.2 M in toluene) and phenylacetylene (439 μL, 4 mmol). The mixture was stirred at ambient temperature for two hours before the system was cooled to −20° C. The mixture was stirred at −20° C. for 10 minutes, followed by the addition of the aldehyde (1 mmol). The reaction mixture was workup after 48 hours by the addition of saturated aq. NH$_4$Cl. The mixture was diluted with 1 N aq. HCl (20 mL), and was extracted with dichloromethane (20 mL×3). The organic extracts were combined, dried over anhydrous Na$_2$SO$_4$ and concentrated to afford the crude product, which was purified on column chromatography to give the corresponding propargylic alcohol. The ee value was determined by HPLC on a chiral stationary phase.

Scheme VI

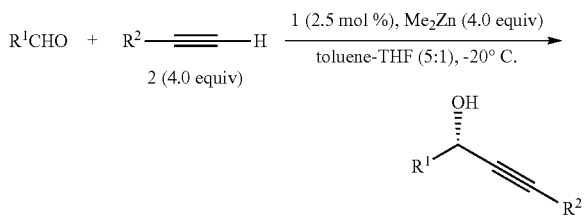

TABLE VI

| Examples | R[1] | R[2] | Compound | Time (h) | Yield[a] (%) | ee[b] (%) |
|---|---|---|---|---|---|---|
| VI-1 | 4-Tol | Ph | (5a) | 72 | 70 | 86 |
| VI-2 | 3-Tol | Ph | (5b) | 72 | 88 | 85 |
| VI-3 | 2-Tol | Ph | (5c) | 72 | 79 | 86 |
| VI-4 | 4-Cl—Ph | Ph | (5d) | 48 | 80 | 86 |
| VI-5 | 3-Cl—Ph | Ph | (5e) | 48 | 82 | 86 |
| VI-6 | 2-Cl—Ph | Ph | (5f) | 48 | 79 | 83 |
| VI-7 | 4-MeO—Ph | Ph | (5g) | 72 | 27[c] | 80 |
| VI-8 | 4-CF3—Ph | Ph | (5h) | 48 | 84 | 87 |
| VI-9 | PhCH=CH— [e] | Ph | (5i) | 48 | 41 | 61 |
| VI-10 | PhCH=C(Me)— [f] | Ph | (5j) | 48 | 21[d] | 71 |
| VI-11 | PhCH2CH2 | Ph | (5k) | 48 | 69 | 49 |
| VI-12 | Ph | 4-CF3—Ph | (5l) | 48 | 46 | 84 |
| VI-13 | Ph | 4-MeO—Ph | (5m) | 48 | 55 | 76 |
| VI-14 | Ph | 4-Cl—Ph | (5n) | 48 | 15 | 66 |
| VI-15 | Ph | n-Bu | (5o) | 48 | 15 | 75 |

[a]Isolated yield after column chromatography, and methylation product was observed in <5% yield in crude 1H NMR in all cases.
[b]Determination by chiral HPLC.
[c]The aldehyde was recovered in 68%.
[d]The aldehyde was recovered in 59%.
[e]The aldehyde used was cinnamaldehyde.
[f]The aldehyde used was α-Me-cinnamaldehyde.

In the cases of substituted benzaldehydes bearing diverse functional groups on the para-, meta-, and ortho-positions, asymmetric alkynylation gave the corresponding propargylic alcohols with 80-87% ee (Examples VI-1 to VI-8). Addition to cinnamaldehyde provided a lower ee (61% ee) of the adduct (Example VI-9), while in the case of the α-substituted analogues, higher ee (71% ee) was observed (Example VI-10). Zinc alkynylides bearing substituents were also utilized, and the corresponding propargylic alcohols were obtained in 66-84% ee, although with unsatisfactory yields (15-55%) (Examples VI-12 to VI-15).

3-Phenyl-1-p-tolyl-prop-2-yn-1-ol (5a)

A white solid (mp. 58-62° C.). $[\alpha]_D^{27}$ −5.2 (c 1.2, CHCl$_3$); $^1$H NMR (400 MHz, CDCl$_3$): δ 7.50-7.43 (m, 4H), 7.32-7.27 (m, 3H), 7.20 (d, J=8.0 Hz, 2H), 5.64 (d, J=6.0 Hz, 1H), 2.36 (s, 3H), 2.21 (d, J=6.0 Hz, 1H); $^{13}$C NMR (100 MHz, CDCl$_3$): δ 137.9 (C), 137.7 (C), 131.6 (CH×2), 129.1 (CH×2), 128.3 (CH), 128.1 (CH×2), 126.6 (CH×2), 122.4 (C), 89.0 (C), 86.3 (C), 64.6 (CH), 21.0 (CH$_3$); IR (neat) 3369, 3053, 3024, 2921, 2864, 2228, 1949, 1904, 1803, 1597, 1489, 1178, 1031, 962, 757, 691 cm$^{-1}$; HRMS calculated for C$_{16}$H$_{14}$O 222.1045, found 222.1049. Chiral HPLC analysis: Chiralcel OD-H, 2-propanol/hexane (10:90), 1.0 mL/min, uv 254 nm; $t_R$=8.5 min (7.0%), 17.4 min (93.0%), 86% ee.

3-Phenyl-1-m-tolyl-prop-2-yn-1-ol (5b)

A colorless, viscous oil. $[\alpha]_D^{27}$ −5.8 (c 1.3, CHCl$_3$); $^1$H NMR (400 MHz, CDCl$_3$): δ 7.48-7.44 (m, 2H), 7.41-7.39 (m, 3H), 7.33-7.24 (m, 4H), 7.16-7.14 (m, 2H), 5.64 (d, J=6.2 Hz, 1H), 2.38 (s, 3H), 2.24 (d, J=6.2 Hz, 1H); $^{13}$C NMR (100 MHz, CDCl$_3$): δ 140.5 (C), 138.1 (C), 131.6 (CH×2), 128.9 (CH), 128.4 (CH), 128.3 (CH), 128.1 (CH×2), 127.3 (CH), 123.7 (CH), 122.4 (C), 89.0 (C), 86.2 (C), 64.7 (CH), 21.2 (CH$_3$); IR (neat) 3368, 3054, 3023, 2920, 2865, 2230, 1951, 1883, 1801, 1607, 1598, 1490, 1032, 757, 691 cm$^{-1}$; HRMS calculated for C$_{16}$H$_{14}$O 222.1045, found 222.1049. Chiral HPLC analysis: Chiralcel OD-H, 2-propanol/hexane (10:90), 1.0 mL/min, uv 254 nm; $t_R$=9.7 min (7.6%), 23.3 min (92.4%), 85% ee.

3-Phenyl-1-o-tolyl-prop-2-yn-1-ol (5c)

A colorless, viscous oil. $[\alpha]_D^{27}$ +12.2 (c 1.2, CHCl$_3$); $^1$H NMR (400 MHz, CDCl$_3$): δ 7.74-7.70 (m, 1H), 7.47-7.42 (m, 2H), 7.32-7.26 (m, 3H), 7.26-7.18 (m, 3H), 5.83 (d, J=5.6 Hz, 1H), 2.49 (s, 3H), 2.18 (d, J=5.6 Hz, 1H); $^{13}$C NMR (100 MHz, CDCl$_3$): δ 138.3 (C), 135.8 (C), 131.6 (CH×2), 130.6 (CH), 128.3 (CH), 128.2 (CH), 128.1 (CH×2), 126.5 (CH), 126.1 (CH), 122.4 (C), 88.6 (C), 86.2 (C), 62.7 (CH), 18.9 (CH$_3$); IR (neat) 3367, 3062, 3023, 2955, 2923, 2862, 2229, 1953, 1886, 1809, 1598, 1489, 1177, 1034, 961, 756, 691 cm$^{-1}$; HRMS calculated for C$_{16}$H$_{14}$O 222.1045, found 222.1053. Chiral HPLC analysis: Chiralcel OD-H, 2-propanol/hexane (10:90), 1.0 mL/min, uv 254 nm; $t_R$=8.3 min (7.0%), 17.8 min (93.0%), 86% ee.

1-(4-Chloro-phenyl)-3-phenyl-prop-2-yn-1-ol (5d)

A white solid (mp. 46-48° C.). $[\alpha]_D^{27}$ −7.9 (c 1.4, CHCl$_3$); $^1$H NMR (400 MHz, CDCl$_3$): δ 7.56-7.53 (m, 2H), 7.46-7.44 (m, 2H), 7.37-7.28 (m, 5H), 5.66 (d, J=6.0 Hz, 1H), 2.30 (d, J=6.0 Hz, 1H); $^{13}$C NMR (100 MHz, CDCl$_3$): δ 139.0 (C), 134.0 (C), 131.6 (CH×2), 128.6 (CH), 128.6 (CH×2), 128.2 (CH×2), 128.0 (CH×2), 122.0 (C), 88.3 (C), 86.7 (C), 64.1 (CH); IR (neat) 3341, 3055, 2873, 2226, 1949, 1903, 1597, 1488, 1090, 1015, 963, 756, 691 cm$^{-1}$; HRMS calculated for C$_{15}$H$_{11}$ClO 242.0498, found 242.0505. Chiral HPLC analysis: Chiralcel OD-H, 2-propanol/hexane (10:90), 1.0 mL/min, uv 254 nm; $t_R$=8.7 min (6.8%), 27.6 min (93.2%), 86% ee.

1-(3-Chloro-phenyl)-3-phenyl-prop-2-yn-1-ol (5e)

A colorless, viscous oil. $[\alpha]_D^{27}$ −14.2 (c 1.5, CHCl$_3$); $^1$H NMR (400 MHz, CDCl$_3$): δ 7.61-7.60 (m, 1H), 7.49-7.45 (m, 3H), 7.33-7.31 (m, 5H), 5.66 (d, J=6.0 Hz, 1H), 2.37-2.35 (m, 1H); $^{13}$C NMR (100 MHz, CDCl$_3$): δ 142.4 (C), 134.2 (C), 131.6 (CH×2), 129.7 (CH), 128.6 (CH), 128.2 (CH), 128.2 (CH×2), 126.7 (CH), 124.7 (CH), 121.9 (C), 88.0 (C), 86.8 (C), 64.0 (CH); IR (neat) 3361, 3062, 3021, 2876, 2230, 1945, 1880, 1808, 1759, 1690, 1597, 1489, 1188, 969, 756 cm$^{-1}$; HRMS calculated for C$_{15}$H$_{11}$ClO 242.0498, found 242.0505. Chiral HPLC analysis: Chiralcel OD-H, 2-propanol/hexane (10:90), 1.0 mL/min, uv 254 nm; $t_R$=8.9 min (7.2%), 29.3 min (92.8%), 86% ee.

1-(2-Chloro-phenyl)-3-phenyl-prop-2-yn-1-ol (5f)

A colorless, viscous oil. $[\alpha]_D^{27}$ +46.2 (c 1.4, CHCl$_3$); $^1$H NMR (400 MHz, CDCl$_3$): δ 7.83-7.81 (m, 1H), 7.48-7.43 (m, 2H), 7.40-7.38 (m, 1H), 7.35-7.25 (m, 5H), 6.03 (d, J=5.6 Hz, 1H), 2.54 (d, J=5.6 Hz, 1H); $^{13}$C NMR (100 MHz, CDCl$_3$): δ 137.8 (C), 132.6 (C), 131.7 (CH×2), 129.6 (CH), 129.5 (CH), 128.5 (CH), 128.3 (CH), 128.2 (CH×2), 127.1 (CH), 122.2 (C), 87.6 (C), 86.4 (C), 62.2 (CH); IR (neat) 3371, 3064, 2928, 2854, 2230, 1953, 1923, 1811, 1597, 1574, 1490, 1442, 1032, 756, 691 cm$^{-1}$; HRMS calculated for C$_{15}$H$_{11}$ClO 242.0498, found 242.0499. Chiral HPLC analysis: Chiralcel OD-H, 2-propanol/hexane (10:90), 0.5 mL/min, uv 254 nm; $t_R$=8.2 min (8.5%), 9.7 min (91.5%), 83% ee.

1-(4-Methoxy-phenyl)-3-phenyl-prop-2-yn-1-ol (5g)

A colorless, viscous oil. $[\alpha]_D^{27}$ −4.2 (c 1.7, CHCl$_3$); $^1$H NMR (400 MHz, CDCl$_3$): δ 7.55-7.51 (m, 2H), 7.47-7.44 (m, 2H), 7.31-7.28 (m, 3H), 6.93-6.89 (m, 2H), 5.63 (d, J=6.0 Hz, 1H), 3.81 (s, 3H), 2.21 (d, J=6.0 Hz, 1H); $^{13}$C NMR (100 MHz, CDCl$_3$): δ 159.4 (C), 132.9 (C), 131.6 (CH×2), 128.3 (CH), 128.1 (CH×2), 128.0 (CH×2), 122.4 (C), 113.8 (CH×2), 89.1 (C), 86.2 (C), 64.3 (CH), 55.1 (CH$_3$); IR (neat) 3412, 3001, 2956, 2934, 2836, 2228, 1610, 1511, 1251, 1173, 1033, 834, 757, 692 cm$^{-1}$; FIRMS calculated for C$_{16}$H$_{14}$O$_2$ 238.0994, found 238.0998. Chiral HPLC analysis: Chiralcel OD-H, 2-propanol/hexane (10:90), 1.0 mL/min, uv 254 nm; $t_R$=11.9 min (10.1%), 26.4 min (89.9%), 80% ee.

3-Phenyl-1-(4-trifluoromethyl-phenyl)-prop-2-yn-1-ol (5h)

A colorless, viscous oil. $[\alpha]_D^{27}$ −6.9 (c 1.4, CHCl$_3$); $^1$H NMR (400 MHz, CDCl$_3$): δ 7.74-7.72 (m, 1H), 7.66-7.64 (m, 1H), 7.47-7.44 (m, 2H), 7.34-7.29 (m, 3H), 5.74 (d, J=5.8 Hz, 1H), 2.39 (d, J=5.8 Hz, 1H); $^{13}$C NMR (100 MHz, CDCl$_3$): δ 144.3 (C), 131.7 (CH×2), 130.3 (q, J=32 Hz, C), 128.8 (CH), 128.3 (CH×2), 126.9 (CH×2), 125.4 (q, J=3.7 Hz, CH×2), 124.0 (q, J=270 Hz, C), 121.9 (C), 88.0 (C), 87.1 (C), 64.2 (CH); IR (neat) 3346, 3063, 2881, 2230, 1916, 1804, 1620, 1490, 1326, 1167, 1127, 1018, 850, 757, 691 cm$^{-1}$; HRMS calculated for C$_{16}$H$_{11}$F$_3$O 276.0762, found 276.0756. Chiral HPLC analysis: Chiralcel OD-H, 2-propanol/hexane (10:90), 1.0 mL/min, uv 254 nm; $t_R$=7.9 min (6.7%), 36.7 min (93.3%), 87% ee.

1,5-Diphenyl-pent-1-en-4-yn-3-ol (5i)

Colorless crystals (mp. 64-65° C.). $[\alpha]_D^{27}$ −7.3 (c 0.5, CHCl$_3$); $^1$H NMR (400 MHz, CDCl$_3$): δ 7.50-7.24 (m, 10H), 6.83 (d, J=15.6 Hz, 1H), 6.42-6.36 (m, 1H), 5.29 (d, J=6.0 Hz, 1H), 2.47 (br, 1H); $^{13}$C NMR (100 MHz, CDCl$_3$): δ 135.9 (C), 131.6 (CH), 131.6 (CH×2), 128.3 (CH×2), 128.3 (CH), 128.1 (CH×2), 127.9 (CH), 127.8 (CH), 126.6 (CH×2), 122.2 (C), 88.1 (C), 86.1 (C), 63.0 (CH); IR (neat) 3349, 3058, 3028, 2914, 2850, 2225, 1952, 1597, 1489, 1443, 1006, 964, 755, 690 cm$^{-1}$; HRMS calculated for C$_{17}$H$_{14}$O 234.1045, found 234.1045. Chiral HPLC analysis: Chiralcel OD-H, 2-propanol/hexane (10:90), 1.5 mL/min, uv 254 nm; $t_R$=9.6 min (19.7%), 30.9 min (80.3%), 61% ee.

2-Methyl-1,5-diphenyl-pent-1-en-4-yn-3-ol (5j)

A colorless, viscous oil. $[\alpha]_D^{27}$+31.6 (c 1.0, CHCl$_3$); $^1$H NMR (400 MHz, CDCl$_3$): δ 7.47-7.44 (m, 2H), 7.36-7.30 (m, 6H), 7.25-7.21 (m, 2H), 6.75 (s, 1H), 5.14 (d, J=5.6 Hz, 1H), 2.09 (d, J=5.6 Hz, 1H), 2.06 (d, J=1.2 Hz, 3H); $^{13}$C NMR (100 MHz, CDCl$_3$): δ 137.0 (C), 136.7 (C), 131.6 (CH×2), 128.9 (CH×2), 128.4 (CH), 128.2 (CH×2), 128.0 (CH×2), 127.1 (CH), 126.7 (CH), 122.4 (C), 88.1 (C), 86.1 (C), 68.6 (CH), 14.1 (CH$_3$); IR (neat) 3415, 3057, 3025, 2917, 2853, 2200, 1616, 1600, 1489, 1443, 1278, 1062, 756, 691 cm$^{-1}$; HRMS calculated for C$_{18}$H$_{16}$O 248.1201, found 248.1194. Chiral HPLC analysis: Chiralcel OD-H, 2-propanol/hexane (10:90), 1.0 mL/min, uv 254 nm; $t_R$=9.0 min (14.4%), 38.6 min (85.6%), 71% ee.

1,5-Diphenyl-pent-1-yn-3-ol (5k)

A colorless, viscous oil. $[\alpha]_D^{27}$+28.4 (c 1.1, CHCl$_3$); $^1$H NMR (400 MHz, CDCl$_3$): δ 7.43-7.41 (m, 2H), 7.31-7.19 (m, 8H), 4.61-4.56 (m, 1H), 2.85 (t, J=8.0 Hz, 2H), 2.14-2.03 (m, 2H), 1.88 (d, J=5.6 Hz, 1H); $^{13}$C NMR (100 MHz, CDCl$_3$): δ 141.2 (C), 131.6 (CH×2), 128.4 (CH×2), 128.3 (CH×2), 128.2 (CH), 128.1 (CH×2), 125.8 (CH), 122.5 (C), 89.9 (C), 85.0 (C), 62.0 (CH), 39.1 (CH$_2$), 31.4 (CH$_2$); IR (neat) 3357, 3027, 2925, 2861, 2230, 1948, 1869, 1600, 1490, 1455, 1338, 1042, 756, 691 cm$^{-1}$; HRMS calculated for C$_{14}$H$_{16}$O 236.1201, found 236.1200. Chiral HPLC analysis: Chiralcel OD-H, 2-propanol/hexane (10:90), 1.0 mL/min, uv 254 nm; $t_R$=11.4 min (25.5%), 22.7 min (74.5%), 49% ee.

1-Phenyl-3-(4-trifluoromethyl-phenyl)-prop-2-yn-1-ol (5l)

Colorless crystals (mp. 50-54° C.). $[\alpha]_D^{27}$+1.3 (c 1.1, CHCl$_3$); $^1$H NMR (400 MHz, CDCl$_3$): δ 7.60-7.52 (m, 5H), 7.43-7.33 (m, 4H), 5.71 (br, 1H), 2.45 (br, 1H); $^{13}$C NMR (100 MHz, CDCl$_3$): δ 140.2 (C), 131.9 (CH×2), 130.3 (q, J=33 Hz, C), 128.7 (CH×2), 128.6 (CH), 126.7 (CH×2), 126.2 (C), 125.2 (q, J=3.7 Hz, CH×2), 123.7 (q, J=271 Hz, C), 91.2 (C), 85.1 (C), 64.9 (CH); IR (neat) 3337, 3066, 3034, 2923, 2237, 1615, 1324, 1168, 1127, 1068, 1018, 842, 698 cm$^{-1}$; HRMS calculated for C$_{16}$H$_{11}$F$_3$O 276.0762, found 276.0752. Chiral HPLC analysis: Chiralcel OD-H, 2-propanol/hexane (10:90), 1.0 mL/min, uv 254 nm; $t_R$=6.9 min (91.9%), 8.3 min (8.1%), 84% ee.

3-(4-Methoxy-phenyl)-1-phenyl-prop-2-yn-1-ol (5m)

A colorless, viscous oil. $[\alpha]_D^{26}$+1.9 (c 1.1, CHCl$_3$); $^1$H NMR (400 MHz, CDCl$_3$): δ 7.61-7.59 (m, 2H), 7.41-7.31 (m, 5H), 6.84-6.82 (m, 2H), 5.66 (d, J=6.0 Hz, 1H), 3.79 (s, 3H), 2.27 (d, J=6.0 Hz, 1H); $^{13}$C NMR (100 MHz, CDCl$_3$): δ 159.3 (C), 140.7 (C), 132.9 (CH×2), 128.2 (CH×2), 127.9 (CH), 126.5 (CH×2), 114.3 (C), 113.6 (CH×2), 87.5 (C), 86.1 (C), 64.5 (CH), 54.9 (CH$_3$); IR (neat) 3401, 3033, 2936, 2838, 2226, 2048, 1890, 1606, 1510, 1249, 1032, 832, 701 cm$^{-1}$; HRMS calculated for C$_{16}$H$_{14}$O$_2$ 238.0994, found 238.0995. Chiral HPLC analysis: Chiralcel OD-H, 2-propanol/hexane (10:90), 1.0 mL/min, uv 254 nm; $t_R$=14.0 min (12.1%), 26.6 min (87.9%), 76% ee.

3-(4-Chloro-phenyl)-1-phenyl-prop-2-yn-1-ol (5n)

A colorless, viscous oil. $[\alpha]_D^{26}$+2.6 (c 1.0, CHCl$_3$); $^1$H NMR (400 MHz, CDCl$_3$): δ 7.59-7.58 (m, 2H), 7.42-7.27 (m, 7H), 5.67 (d, J=6.0 Hz, 1H), 2.31 (d, J=6.0 Hz, 1H); $^{13}$C NMR (100 MHz, CDCl$_3$): δ 140.3 (C), 134.3 (C), 132.8 (CH×2), 128.43 (CH×2), 128.38 (CH×2), 128.2 (CH), 126.5 (CH×2), 120.7 (C), 89.8 (C), 85.2 (C), 64.6 (CH); IR (neat) 3360, 3065, 2875, 2230, 1956, 1901, 1593, 1488, 1190, 1092, 1015, 963, 828 698 cm$^{-1}$; HRMS calculated for C$_{15}$H$_{11}$ClO 242.0498, found 242.0500. Chiral HPLC analysis: Chiralcel OD-H, 2-propanol/hexane (10:90), 0.5 mL/min, uv 254 nm; $t_R$=17.3 min (82.8%), 19.0 min (17.2%), 66% ee.

1-Phenyl-hept-2-yn-1-ol (5o)

A colorless oil. $[\alpha]_D^{25}$−18.1 (c 1.3, CHCl$_3$); $^1$H NMR (400 MHz, CDCl$_3$): δ 7.54-7.52 (m, 2H), 7.38-7.28 (m, 3H), 5.43 (d, J=5.6 Hz, 1H), 2.26 (td, J=7.2, 2.0 Hz, 2H), 2.13 (d, J=5.6 Hz, 1H), 1.55-1.36 (m, 4H), 0.898 (t, J=7.2 Hz, 3H); $^{13}$C NMR (100 MHz, CDCl$_3$): δ 141.2 (C), 128.3 (CH×2), 127.9 (CH), 126.5 (CH×2), 87.3 (C), 79.9 (C), 64.5 (CH), 30.5 (CH$_2$), 21.8 (CH$_2$), 18.3 (CH$_2$), 13.4 (CH$_3$); IR (neat) 3397, 3031, 2958, 2933, 2873, 2227, 1950, 1884, 1809, 1603, 1494, 1455, 1135, 1002, 698 cm$^{-1}$; HRMS calculated for C$_{13}$H$_{16}$O 188.1201, found 188.1192. Chiral HPLC analysis: Chiralcel OD-H, 2-propanol/hexane (10:90), 1.0 mL/min, uv 254 nm; $t_R$=11.0 min (87.5%), 13.8 min (12.5%), 75% ee.

In conclusion, the asymmetric addition of zinc alkynylides to aldehydes to give optically active propargylic alcohols catalyzed by ligand 1 has been developed, affording the products in 49-87% ee. Notably, this catalytic system required only 2.5 mol % of the chiral ligand to afford propargylic alcohols derived from substituted benzaldehydes with >80% ee without additional additives. To the best of our knowledge, ligand 1 is the first chiral mediator bearing a β-amino thiol reported to catalyze the alkynylzinc addition reaction with aldehydes.

Although the present invention has been explained in relation to its preferred embodiment, it is to be understood that many other possible modifications and variations can be made without departing from the scope of the invention as hereinafter claimed.

What is claimed is:

1. A method for preparing a propargylic alcohol catalyzed by 2-morpholinoisobornane-10-thiol (MITH), comprising reacting R$_1$CHO with R$_2$CCH in the presence of R$_3$ZnR$_4$ and MITH, wherein
   each of R$_1$, R$_2$, R$_3$, and R$_4$, independently, is optionally substituted alkyl, alkenyl, cycloalkyl, cycloalkenyl, alkylsilyl, heterocycloalkyl, heterocycloalkenyl, aryl, aryloxy, or heteroaryl.

2. The method as claimed in claim 1, wherein
   each of R$_1$ and R$_2$, independently, is C$_{1-30}$ alkyl optionally substituted by one or more of halogen, nitro, cyano, 5-14 membered heteroaryl, C$_{6-14}$ aryl, C$_{6-14}$ aryloxy, C$_{1-30}$ alkoxy, $C_{1-30}$ haloalkyl, $CO_2$—$C_{1-30}$ alkyl, $CO_2$—$C_{2-30}$ alkenyl, and $C_{1-30}$ alkylsilyloxy; $(CH_2)_iR_a$; $C_{2-30}$ alkenyl optionally substituted by one or more of halogen, nitro, cyano, 5-14 membered heteroaryl, $C_{6-14}$ aryl, $C_{6-14}$ aryloxy, $C_{1-30}$ alkoxy, $C_{1-30}$ haloalkyl, $CO_2$—$C_{1-30}$ alkyl and $CO_2$—$C_{2-30}$ alkenyl; $(CH_2)_rCH=CH(CH_2)_kR_a$; $C_{5-14}$ cycloalkyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; $C_{5-14}$ cycloalkenyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; 5-14 membered heterocycloalkyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; 5-14 membered heterocycloalkenyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; $C_{6-14}$ aryl optionally substituted by one or more of halogen, nitro, cyano, $C_{1-30}$ alkyl, $C_{2-30}$ alkenyl, $C_{1-30}$ alkoxy, $C_{1-30}$ haloalkyl, $C_{6-14}$ aryloxy, $CO_2$—$C_{1-30}$ alkyl, and $CO_2$—$C_{2-30}$ alkenyl; $C_{1-30}$ alkylsilyl optionally substituted by one or more of halogen, nitro, and cyano; or 5-14 membered heteroaryl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl, and $CO_2$—$C_{2-30}$ alkenyl; and each of $R_3$ and $R_4$ independently is $C_{1-30}$ alkyl optionally substituted by one or more of halogen, nitro, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and 5-14 membered heteroaryl; $C_{2-30}$ alkenyl optionally substituted by one or more of halogen, nitro, cyano, $C_{1-30}$ alkoxy, $C_{1-30}$ haloalkyl, $CO_2$—$C_{1-30}$ alkyl, $CO_2$—$C_{2-30}$ alkenyl, $C_{6-14}$ aryl and $C_{5-14}$ heteroaryl; $C_{5-14}$ cycloalkyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; $C_{5-14}$ cycloalkenyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; 5-14 membered heterocycloalkyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; 5-14 membered heterocycloalkenyl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; $C_{6-14}$ aryl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; or 5-14 membered heteroaryl optionally substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl, wherein $R_a$ is $C_{6-14}$ aryl substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl; $C_{1-30}$ alkylsilane optionally substituted by one or more of halogen, nitro, cyano, $C_{1-30}$ alkoxy, $CO_2$—$C_{1-30}$ alkyl, and $CO_2$—$C_{2-30}$ alkenyl; or 5-14 membered heteroaryl substituted by one or more of halogen, nitro, cyano, $C_{1-30}$ alkyl, $C_{2-30}$ alkenyl, $C_{1-30}$ alkoxy, $C_{1-30}$ haloalkyl, $CO_2$—$C_{1-30}$ alkyl and $CO_2$—$C_{2-30}$ alkenyl;

i is an integer of 1 to 30; and each of r and k independently is an integer of 0 to 30.

3. The method as claimed in claim 1, each of $R_1$ and $R_2$, independently, is $C_{1-16}$ alkyl optionally substituted by one or more of halogen, nitro, cyano, 5-14 membered heteroaryl, $C_{6-14}$ aryl, $C_{6-14}$ aryloxy, $C_{1-16}$ alkoxy, $C_{1-16}$ haloalkyl, $CO_2$—$C_{1-16}$ alkyl, $CO_2$—$C_{2-16}$ alkenyl, and $C_{1-16}$ alkylsilyloxy; $(CH_2)_iR_a$; $C_{2-16}$ alkenyl optionally substituted by one or more of halogen, nitro, cyano, 5-14 membered heteroaryl, $C_{6-14}$ aryl, $C_{6-14}$ aryloxy, $C_{1-16}$ alkoxy, $C_{1-16}$ haloalkyl, $CO_2$—$C_{1-16}$ alkyl and $CO_2$—$C_{2-16}$ alkenyl; $(CH_2)_rCH=CH(CH_2)_kR_a$, $C_{5-14}$ cycloalkyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; $C_{5-14}$ cycloalkenyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; 5-14 membered heterocycloalkyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; 5-14 membered heterocycloalkenyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; $C_{6-14}$ aryl optionally substituted by one or more of halogen, nitro, cyano, $C_{1-16}$ alkyl, $C_{2-16}$ alkenyl, $C_{1-16}$ alkoxy, $C_{1-16}$ haloalkyl, $C_{6-14}$ aryloxy, $CO_2$—$C_{1-16}$ alkyl, and $CO_2$—$C_{2-16}$ alkenyl; $C_{1-16}$ alkylsilyl optionally substituted by one or more of halogen, nitro, and cyano; or 5-14 membered heteroaryl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl, and $CO_2$—$C_{2-16}$ alkenyl; and each of $R_3$ and $R_4$ independently is $C_{1-16}$ alkyl optionally substituted by one or more of halogen, nitro, cyano, $C_{1-16}$ alkoxy, $C_{1-16}$ haloalkyl, $CO_2$—$C_{1-16}$ alkyl, $CO_2$—$C_{2-16}$ alkenyl, $C_{6-14}$ aryl and 5-14 membered heteroaryl; $C_{2-16}$ alkenyl optionally substituted by one or more of halogen, nitro, cyano, $C_{1-16}$ alkoxy, $C_{1-16}$ haloalkyl, $CO_2$—$C_{1-16}$ alkyl, $CO_2$—$C_{2-16}$ alkenyl, $C_{6-14}$ aryl and $C_{5-14}$ heteroaryl; $C_{5-14}$ cycloalkyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; $C_{5-14}$ cycloalkenyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; 5-14 membered heterocycloalkyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; 5-14 membered heterocycloalkenyl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; $C_{6-14}$ aryl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; or 5-14 membered heteroaryl optionally substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl, wherein $R_a$ is $C_{6-14}$ aryl substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl; $C_{1-16}$ alkylsilane optionally substituted by one or more of halogen, nitro, cyano, $C_{1-16}$ alkoxy, $CO_2$—$C_{1-16}$ alkyl, and $CO_2$—$C_{2-16}$ alkenyl; or 5-14 membered heteroaryl substituted by one or more of halogen, nitro, cyano, $C_{1-16}$ alkyl, $C_{2-16}$ alkenyl, $C_{1-16}$ alkoxy, $C_{1-16}$ haloalkyl, $CO_2$—$C_{1-16}$ alkyl and $CO_2$—$C_{2-16}$ alkenyl;

i is an integer of 1 to 16; and each of r and k independently is an integer of 0 to 16.

4. The method as claimed in claim 3, wherein $R_2$ is $C_{6-14}$ aryl optionally substituted by one or more of halogen, $C_{1-16}$ haloalkyl, and $C_{1-16}$ alkoxy.

5. The method as claimed in claim 4, wherein $R_1$ is $(CH_2)_i R_a$, in which $R_a$ is $C_{6-14}$ aryl and i is an integer of 1 to 5.

6. The method as claimed in claim 4, wherein $R_1$ is $C_{6-14}$ aryl optionally substituted by one or more of halogen, $C_{1-16}$ haloalkyl, and $C_{1-16}$ alkoxy.

7. The method as claimed in claim 4, wherein $R_1$ is $(CH_2)_r CH=CH(CH_2)_k R_a$, in which $R_a$ is $C_{6-14}$ aryl, and r and k respectively are 1 and 0.

8. The method as claimed in claim 4, wherein $R_1$ is $C_{2-16}$ alkenyl optionally substituted by one or more of $C_{6-14}$ aryl and $C_{1-16}$ alkyl.

9. The method as claimed in claim 3, wherein $R_2$ is $C_{1-16}$ alkyl.

10. The method as claimed in claim 9, wherein $R_1$ is $C_{6-14}$ aryl.

11. The method as claimed in claim 1, wherein a solvent used is selected from a group consisting of toluene, hexane, hexane-tetrahydrofuran, toluene-dichloromethane, toluene-dioxane, toluene-diethyl ether, and toluene-tetrahydrofuran.

12. The method as claimed in claim 11, wherein the toluene-tetrahydrofuran is used as the solvent.

13. The method as claimed in claim 12, wherein a volume ratio of toluene to tetrahydrofuran is in a range from 0.5 to 10.

14. The method as claimed in claim 1, wherein a molar ratio of $R_3ZnR_4$ to $R_2CCH$ is in a range from 0.25 to 4.

15. The method as claimed in claim 1, wherein $R_2CCH$ is reacted first with $R_3ZnR_4$ and then with $R_1CHO$.

16. The method as claimed in claim 15, wherein a temperature of the reaction with $R_3ZnR_4$ is controlled in a range from 10° C. to 70° C.

17. The method as claimed in claim 16, wherein a temperature of the reaction with $R_1CHO$ is controlled in a range from −30° C. to 40° C.

18. The method as claimed in claim 1, wherein MITH is used in an amount of 0.1~10 mol % based on $R_2CCH$.

19. The method as claimed in claim 1, wherein (−)-2-exo-morpholinoisobornane-10-thiol((−)-MITH) is used as MITH.

20. The method as claimed in claim 1, wherein $R_2CCH$ and $R_3ZnR_4$ are respectively used in an amount of 1 to 8 equivalents based on $R_1CHO$.

* * * * *